US010317366B2

United States Patent
Yasuno et al.

(10) Patent No.: US 10,317,366 B2
(45) Date of Patent: Jun. 11, 2019

(54) ION MOBILITY SPECTROMETER

(71) Applicant: SHIMADZU CORPORATION, Kyoto-shi, Kyoto (JP)

(72) Inventors: Motohide Yasuno, Kyoto (JP); Akiko Imazu, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/758,609

(22) PCT Filed: Sep. 9, 2015

(86) PCT No.: PCT/JP2015/075643
§ 371 (c)(1),
(2) Date: Jul. 30, 2018

(87) PCT Pub. No.: WO2017/042918
PCT Pub. Date: Mar. 16, 2017

(65) Prior Publication Data
US 2018/0328886 A1 Nov. 15, 2018

(51) Int. Cl.
*H01J 49/00* (2006.01)
*G01N 27/68* (2006.01)
(Continued)

(52) U.S. Cl.
CPC .......... *G01N 27/68* (2013.01); *G01N 27/622* (2013.01); *H01J 49/10* (2013.01); *H01J 49/40* (2013.01)

(58) Field of Classification Search
CPC ........ H01J 49/00; H01J 49/0027; H01J 49/02; H01J 49/06; H01J 49/061; H01J 49/062;
(Continued)

(56) References Cited

U.S. PATENT DOCUMENTS 8,173,959 B1* 5/2012 Boumsellek ......... G01N 27/622
250/281
2011/0095175 A1* 4/2011 Bateman .............. G01N 27/624
250/282
(Continued)

FOREIGN PATENT DOCUMENTS

JP 2005-174619 A 6/2005

OTHER PUBLICATIONS

Robert R. Hudgins, et al., "High-resolution ion mobility measurements for silicon cluster anions and cations", Journal of Chemical Physics, Nov. 1, 1999, pp. 7865-7870, vol. 111, No. 17.
(Continued)

*Primary Examiner* — Jason L McCormack
(74) *Attorney, Agent, or Firm* — Sughrue Mion, PLLC

(57) ABSTRACT

A first shutter gate is disposed at an entrance of a drift region, and a second shutter gate is disposed on the downstream side in an ion-drifting direction. In a high-resolution measurement mode, a controller (9) controls voltage generators to open the second shutter gate to collect ions into a pulsed form at the first shutter gate. In this mode, the controller controls the voltage generators to open the first shutter gate to collect ions into a pulsed form at the second shutter gate. In a zoom-in measurement mode where ions within a specified range of ion mobility are measured with high resolving power, the controller controls the voltage generators to open the first shutter gate for a short period of time, and then to open the second shutter gate for a short period of time after a lapse of a predetermined time period.

5 Claims, 2 Drawing Sheets

(51) Int. Cl.
*G01N 27/62* (2006.01)
*H01J 49/10* (2006.01)
*H01J 49/40* (2006.01)

(58) Field of Classification Search
CPC ..... H01J 49/065; G01N 27/62; G01N 27/622; G01N 27/624; G01N 27/68
USPC ................................ 250/281, 282, 283, 293
See application file for complete search history.

(56) References Cited

U.S. PATENT DOCUMENTS

2012/0326023 A1* 12/2012 Kozole ................ G01N 27/622
250/282
2016/0005581 A1* 1/2016 Graichen ............. G01N 27/622
250/282

OTHER PUBLICATIONS

Written Opinion for PCT/JP2015/075643 dated Dec. 15, 2015 [PCT/ISA/237].
International Preliminary Report on Patentability for PCT/JP2015/075643 dated Mar. 13, 2018 [PCT/IB/373].

* cited by examiner $T2 = T1 \times (L2/L1)$
$T1 = L1/v_{min} = L1 / (K_{min} \times E)$ $T_p = L1 / (K_p \times E)$

ION MOBILITY SPECTROMETER

CROSS REFERENCE TO RELATED APPLICATIONS

This application is a National Stage of International Application No. PCT/JP2015/075643, filed on Sep. 9, 2015.

TECHNICAL FIELD

The present invention relates to an ion mobility spectrometer for separating and detecting ions according to their mobility, or for separating ions and sending them to a mass spectrometer unit or other units at a later stage.

BACKGROUND ART

When a molecular ion generated from a sample molecule is made to move in a gas medium under the effect of an electric field, the ion moves at a speed proportional to its mobility which is determined by the intensity of the electric field, size of the molecule and other factors. Ion mobility spectrometry (IMS) is a measurement method in which this mobility is utilized for an analysis of sample molecules. FIG. 5 is a schematic configuration diagram of a conventional and common type of ion mobility spectrometer (for example, see Patent Literature 1).

This ion mobility spectrometer includes: an ion source 1 for ionizing component molecules in a sample; a drift region 5 which is provided, for example, within a cylindrical housing (not shown), for measuring the ion mobility; and a detector 6 for detecting ions which have traveled through the drift region 5. Additionally, in order to send the ions generated in the ion source 1 into the drift region 5 in a pulsed form during a limited short time width, a shutter gate 3 is provided at an entrance of the drift region 5. The atmosphere inside the housing is maintained at atmospheric pressure or low vacuum of approximately 100 [Pa]. A uniform electric field having a downward potential gradient (for drifting ions) in the moving direction of the ions (in FIG. 5, the Z-direction) is formed within the drift region 5 by DC voltages respectively applied to a number of ring-shaped electrodes 2a included in a drift-electrode group 2 arranged within the drift region 5. A flow of neutral gas is formed in the opposite direction to the direction of the drift motion by the electric field. In order to reduce an image current induced in a detection electrode of the detector 6 by ions drifting with drift motion, the electrode 2a disposed at the final stage preceding the detector 6 employs a grid-type (mesh type) electrode.

The ions generated in the ion source 1 are temporarily blocked by the shutter gate 3. The shutter gate 3 is subsequently opened for a short period of time, whereupon the ions in a packet-like form are introduced into the drift region 5. Colliding with the counterflowing gas within the drift region 5, the introduced ions are driven forward by the electric field. Those ions are temporally separated according to their ion mobilities, which depend on the size, steric structure, electric charge and other properties of the individual ions. Accordingly, ions with different ion mobilities reach the detector 6 demonstrating certain intervals of time. If the electric field within the drift region 5 is uniform, the collision cross-section between an ion and the counterflowing gas can be estimated from the drift time required for the ion to pass through the drift region 5.

The capability to separate a certain kind of ions originating from a sample molecule can be evaluated by the resolving power R calculated by the following formula (1):

$$R = Td/\Delta T \quad (1)$$

where Td is the drift time required for the ion to travel in the drift region 5 and $\Delta T$ is the pulse width (temporal spread) of the ions at the time when the ions are detected in the detector 6.

A high-resolution ion mobility spectrometer with high resolving power R is required for separating molecules having molecular weights close to each other or for separating molecules having the same molecular weight but different molecular structures (structural isomers). For increasing the resolving power R, the drift time Td should be increased or the ion pulse width $\Delta T$ should be decreased, as is evident from the formula (1). To decrease the ion pulse width $\Delta T$, the shutter open time should be shortened. However, shortening the shutter open time decreases the amount of ions passing through the shutter and causes the sensitivity to deteriorate. Thus, there is a limit in shortening the shutter open time if a certain level of sensitivity is demanded. In addition, even ions having the same ion mobility spread in the front-back direction while travelling through the drift region, due to the diffusion (spatial spread of molecules due to their random motion), dispersion (spatial spread of molecules during their motion in a fluid), or other actions. Thus, there is also a certain lower limit of the ion pulse width $\Delta T$ even if the shutter open time is shortened. In view of the above, an effective method for increasing the resolving power in an ion mobility spectrometer is to increase the length of the drift region 5, i.e., the drift length L.

However, in the ion mobility spectrometer, it is necessary to close the shutter gate 3 until all ions introduced in the drift region 5 completely pass through the drift region 5, in order to avoid the situation in which ions with high drift speeds overlap ions with low drift speeds during the measurement. In view of this, if the drift time Td is increased due to the increase of the drift length L as mentioned above, the waiting time also needs to be increased, which is the period of time from a time point when the shutter gate 3 is opened to a time point when the shutter gate 3 is next opened after the previous opening. In other words, an operation period of the shutter gate becomes longer, which results in a decrease in the rate at which the measurement for the ion mobility spectrum can be performed per one second (sampling rate).

Non Patent Literature 1 discloses, for example, that a high-resolution ion mobility spectrometer including a drift tube with a length of 63 cm is used to perform isomer separation on silicon clusters. A typical ion mobility spectrum thereby measured has a significantly long drift time of approximately 100 msec. In this case, the sampling rate is 10 Hz. In a case where the ion mobility spectrometer is used as a detector of a liquid chromatograph (LC) to analyze components in a sample which are sequentially eluted from a column of the LC, a decrease in the sampling rate results in a longer time interval between data points in the chromatogram. This may possibly prevent a peak from being appropriately captured. In an extreme case, some specific ion may be omitted from detection.

CITATION LIST

Patent Literature

Patent Literature 1: JP 2005-174619 A

Non-Patent Literature

Non-Patent Literature 1: Robert R. H. and two other authors, "High-resolution ion mobility measurements for silicon cluster anions and cations", *JOURNAL OF CHEMICAL PHYSICS*, 1999, Vol. 111, No. 17, pp. 7865-7870

SUMMARY OF INVENTION

Technical Problem

In an ion mobility spectrometer, the resolving power R and sampling rate S generally have the trade-off relationship. Thus, it is difficult to achieve both a high resolving power and high sampling rate in a single device. The present invention has been developed to solve such a problem, and its primary objective is to provide an ion mobility spectrometer capable of switching between a high-resolution measurement and high-sampling-rate measurement according to the purpose of analysis or other factors.

Solution to Problem

The present invention developed for solving the previously described problem is an ion mobility spectrometer in which ions in a packet-like form are introduced into and made to drifted through a drift region in which an electric field is formed to separate the ions according to their ion mobilities, the ion mobility spectrometer including:

a) a first shutter gate disposed at an entrance of the drift region;

b) a second shutter gate disposed on the downstream side of the first shutter gate in the drifting direction in the drift region;

c) a voltage generator for applying predetermined voltages respectively to the first and second shutter gates; and d) a controller for controlling the voltage generator so as to apply voltages to the first shutter gate and the second shutter gate so that ions are made to pass through the first shutter gate in a pulsed form and to directly pass through the second shutter gate in a first measurement mode (high-resolution measurement mode), hile ions are made to directly pass through the first shutter gate and to pass through the second shutter gate in a pulsed form in a second measurement mode (high-sampling-rate measurement mode).

In the ion mobility spectrometer according to the present invention, ions separated according to their ion mobilities during their drift through the drift region may be detected by the detector. Alternatively, ions separated according to their ion mobilities may be further introduced in a mass separator or the like that separates ions according to their mass-to-charge ratios, for example.

For example, in a case where ions that have passed through the drift region are detected by a detector, the length of the drift region between the first shutter gate and the detector is longer than the length of the drift region between the second shutter gate and the detector. In view of this, the controller of the ion mobility spectrometer according to the present invention conducts measurements in two modes: In the first measurement mode (high-resolution measurement mode), the controller sets the voltage to be applied to each of the first and second shutter gates so that only the first shutter gate on the upstream side temporarily blocks ions and then allows them to pass through for a short period of time while the second shutter gate on the downstream side does not block ions at all. In this case, the drift length is longer than in the second measurement mode, which means that the drift time is longer and the resolving power is correspondingly higher. In the second measurement mode (high sampling-rate measurement mode), the controller sets the voltage to be applied to each of the first and second shutter gates so that only the second shutter gate on the downstream side temporarily blocks ions and then allows them to pass through for a short period of time while the first shutter gate on the upstream side does not block ions at all. In this case, the drift length is shorter than in the first measurement mode, and thus the drift time is also shorter. Although the resolving power is relatively low, the operation period of the second shutter gate can be shortened to increase the sampling rate.

The ion mobility spectrometer according to the present invention may further include an instruction section for instructing the controller to select at least one of the first measurement mode and the second measurement mode, and the controller may perform a control corresponding to the first measurement mode or the second measurement mode according to a selection instruction by the instruction section.

In a preferable configuration of the ion mobility spectrometer according to the present invention, a third measurement mode (zoom-in measurement mode) is provided in addition to the first and the second measurement modes, and the controller in the third measurement mode controls the voltage generator to apply voltages to the first shutter gate and the second shutter gate so that the first shutter gate makes ions pass through in the pulsed form, and the second shutter gate makes ions pass through in the pulsed form for a predetermined time period after the passage of a predetermined time period from a time point when the first shutter gate is opened.

In the third measurement mode, the ions that have passed through the first shutter gate for a short period of time so as to be in the packet-like form are separated to a certain degree according to their ion mobilities in the drift region from the first shutter gate to the second shutter gate. Among them, only ions within a specified range of ion mobility (or drift time) pass through the second shutter gate to further drift in the drift region so as to be separated. Accordingly, the resolving power in the third measurement mode is almost equal to that of the first measurement mode. In the third measurement mode, ions within a specific range of ion mobility and not the entire range can be detected by, for example, the detector to create an ion mobility spectrum. Ions which do not fall within that specific range of ion mobility are blocked at the second shutter gate. Therefore, although this depends upon the range of ion mobilities of the ions to be measured, the drift time becomes shorter than in the case where all ions are to be measured, so that the sampling rate can be increased. In other words, limiting the range of ions to be subjected to the measurement makes it possible to set a higher sampling rate than in the first measurement mode while achieving almost the same level of high resolving power as in the first measurement mode.

In the ion mobility spectrometer according to the present invention, another shutter gate may be provided in addition to the first and the second shutter gates, leaving a space in the ion-drifting direction. In other words, three or more shutter gates may be provided, and voltages to be applied thereto may appropriately be switched.

Advantageous Effects of the Invention

With the ion mobility spectrometer according to the present invention, the following measurement modes can be selectively performed according to the purpose of an analysis using a single device: (i) a measurement mode in which ions generated from a sample can be separated with high resolving power, although the sampling rate deteriorates, and (ii) a measurement mode in which the sampling rate can be increased to increase the frequency of repeating measurements, i.e., to shorten the time interval of the measurement, although the resolving power deteriorates. This enables, for example, an analysis of molecules which are identical in molecular weight but different in molecular structure. In addition, an omission of the detection of components as well as a distortion of the peak shape can be reduced even in a case where samples are sequentially supplied as in a device which is used as a detector for an LC.

Furthermore, according to a preferable configuration of the present invention, an ion mobility spectrum having an appropriate width before and after an ion mobility which is particularly worthy of attention can be obtained with high resolving power. The sampling rate can also be increased in such a case.

DESCRIPTION OF EMBODIMENTS

An embodiment of the ion mobility spectrometer according to the present invention is described as follows, with reference to the attached drawings.

Figure 1:
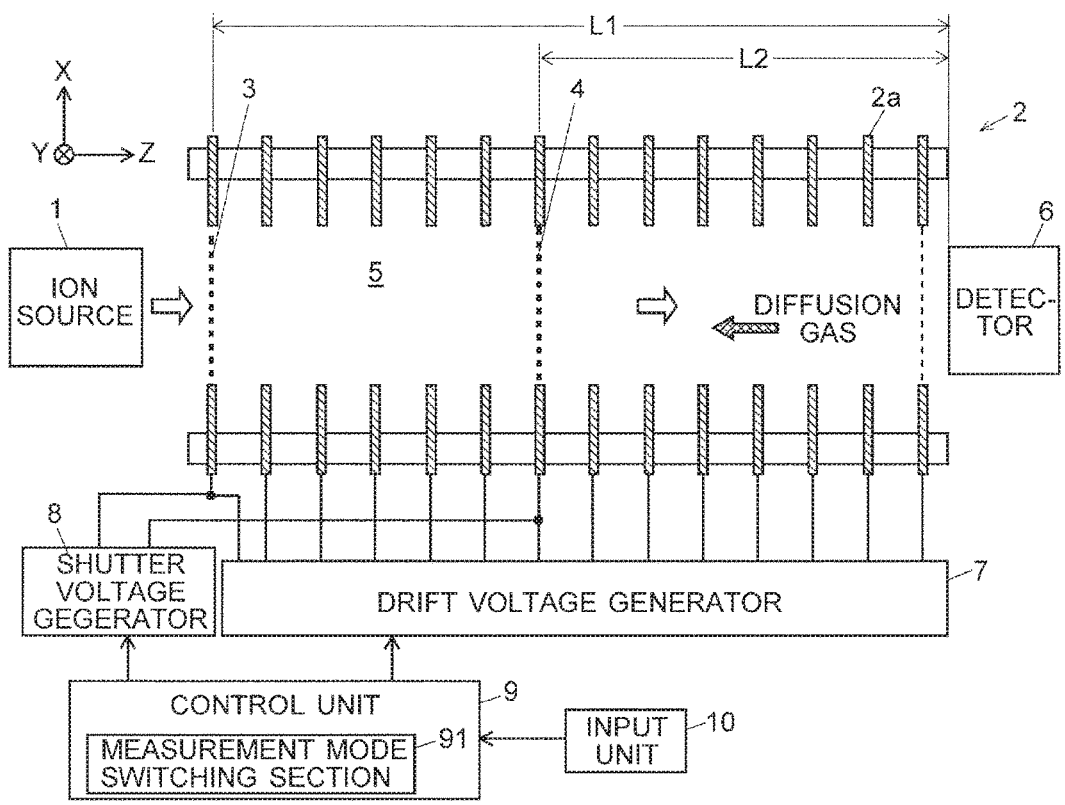
FIG. 1 is a schematic configuration diagram showing an ion mobility spectrometer according to an embodiment of the present invention.
Figure 5:
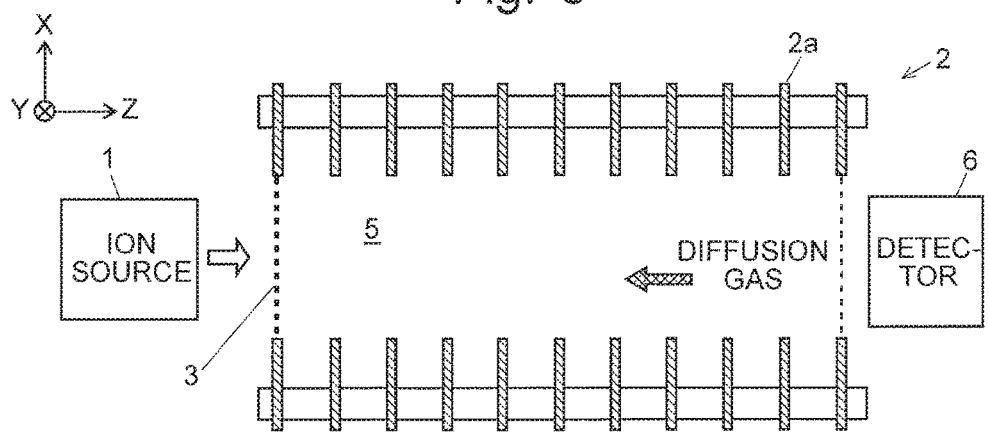
FIG. 5 is a schematic configuration diagram showing a typical ion mobility spectrometer.

FIG. 1 is a schematic sectional diagram showing an ion mobility spectrometer according to the present embodiment. Components which are identical or corresponding to those included in a conventional ion mobility spectrometer already described with reference to FIG. 5 are denoted by the same reference signs as those used for the conventional ion mobility spectrometer.

The ion mobility spectrometer according to the present embodiment includes: a first shutter gate 3 disposed at an entrance of a drift region 5; and a second shutter gate 4 disposed in the drift region 5 on the downstream side of the shutter gate 3 in the ion-drifting direction. A drift voltage generator 7 applies predetermined direct-current voltages respectively to a plurality of electrodes 2a in a drift electrode group 2. A shutter voltage generator 8 applies pulsed voltages respectively to the first and second shutter gates 3 and 4 at each predetermined timing. A controller 9 includes a measurement mode switching section 91 as a functional block to control each of the drift voltage generator 7 and the shutter voltage generator 8. An input unit 10 is connected to the controller 9. A user (analysis operator) can perform the selection of a measurement mode and other operations using the input unit 10.

Hereinafter, let L1 denote the distance from the first shutter gate 3 to a detection electrode 6a at the entrance end of a detector 6, and L2 denote the distance from the second shutter gate 4 to the detection electrode 6a (L2<L1). In the ion mobility spectrometer according to the present embodiment, the measurement mode can be selectively designated using the input unit 10, from three measurement modes including a high-resolution measurement mode, a high sampling-rate measurement mode, and a zoom-in measurement mode. The operation in each of the measurement modes is described with reference to FIGS. 2A to 4B.

[High-Resolution Measurement Mode]

Figure 2A:
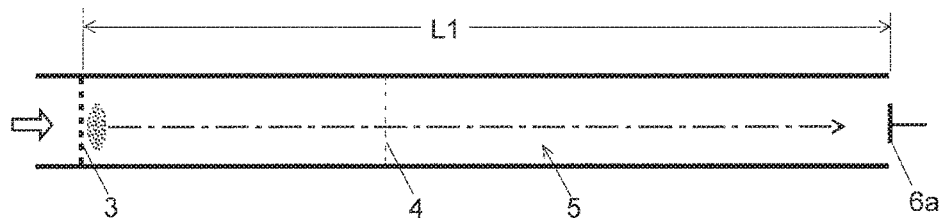
FIG. 2A is a schematic configuration diagram for explaining an operation in the ion mobility spectrometer according to the present embodiment in a high-resolution measurement mode.
Figure 2B:
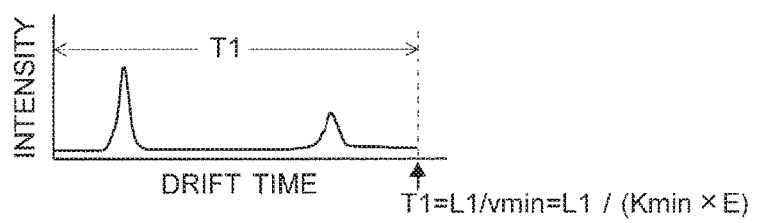
FIG. 2B is a schematic diagram showing an ion mobility spectrum in the high-resolution measurement mode.

FIGS. 2A and 2B are explanatory diagrams for explaining an operation in the high-resolution measurement mode. FIG. 2A is a schematic configuration diagram, and FIG. 2B is a schematic diagram showing an ion mobility spectrum.

When the high-resolution measurement mode is selected, the measurement mode switching section 91 of the controller 9 controls the voltage generators 7 and 8 so as to make the second shutter gate 4 be constantly opened and the first shutter gate 3 collect ions into a pulsed form. In other words, the second shutter gate 4 does not function as the shutter gate but merely forms a uniform acceleration electric field, like other electrodes 2a. In this case, the packet of ions collected at the first shutter gate 3 drift through the entire drift region 5 of drift length L1, and then arrive at the detector 6. The long drift length means a long drift time for the ions, thereby enabling a high-resolution measurement. In this measurement mode, a time width during which the first shutter gate 3 is opened affects the resolving power. In order to obtain a high level of resolving power, the time period during which the first shutter gate 3 is opened should preferably be as short as possible within a permissible range of the signal intensity.

In the drift region 5 where the intensity of the electric field is E, each ion moves at a drift speed v proportional to mobility K which is unique to the molecular species (molecular structure) of the ion: $v=K\times E$. For ions having larger molecular weight and more-complicated molecular structures, the value of the mobility K becomes smaller. This increases the time required for the ions to travel through a certain drift length. If the minimum ion mobility of a molecule to be measured (i.e., a target molecule for which the ion mobility spectrum should be obtained) is Kmin, the ion mobility measurement should be performed to detect ions with drift times ranging from 0 to T1 where, $T1=L1/vmin=L1/(Kmin\times E)$.

In this measurement mode, the entire drift region 5 is used, to allow for an ion mobility analysis with high resolving power. However, this mode requires the shutter gate 3 to be closed during time T1 in which all ions to be subjected to the measurement travels through the entire drift region 5, in order to avoid the situation in which ions with high drift speeds overlap ions with low drift speeds during the measurement. This elongates the time period required for measuring a single ion mobility spectrum. As a result, the sampling rate, calculated by $S=1/T1$, becomes low due to the elongated drift time.

[High Sampling-Rate Measurement Mode]

Figure 3A:
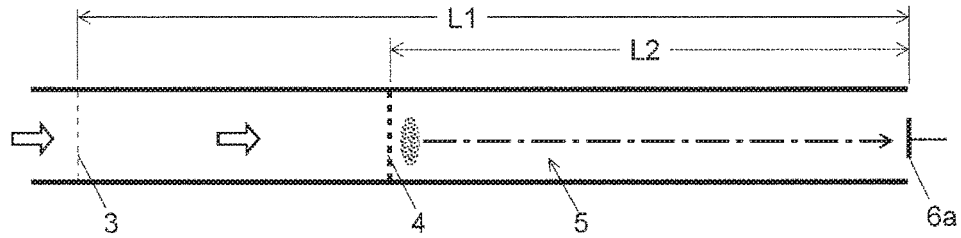
FIG. 3A is a schematic configuration diagram for explaining an operation in the ion mobility spectrometer according to the present embodiment in a high sampling-rate measurement mode.
Figure 3B:
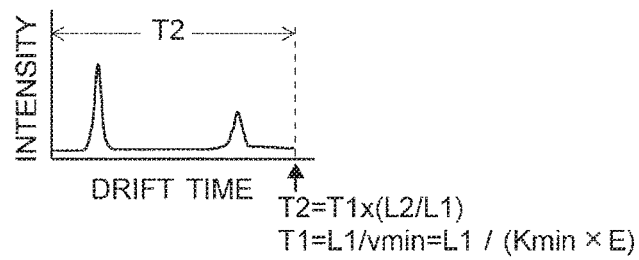
FIG. 3B is a schematic diagram showing an ion mobility spectrum in the high sampling-rate measurement mode.

FIGS. 3A and 3B are explanatory diagrams for explaining an operation in the high sampling-rate measurement mode. FIG. 3A is a schematic configuration diagram, and FIG. 3B is a schematic diagram showing an ion mobility spectrum.

When the high sampling-rate measurement mode is selected, the measurement mode switching section 91 of the controller 9 controls the voltage generators 7 and 8 so as to make the first shutter gate 3 be constantly opened and the second shutter gate 4 collect ions into a pulsed form. In this case, the packet of ions collected at the second shutter gate 4 drift through an area of drift length L2 forming a portion of the drift region 5, and then arrive at the detector 6. The drift length is shorter than in the high-resolution measurement mode, so that the drift time is also shorter.

If the intensity of the electric field in the drift region 5 is E that is the same as in the high-resolution measurement mode, the drift time T2 can be expressed as T2=T1×(L2/L1). Specifically, the time required for a single measurement of the ion mobility spectrum is shortened by a factor of L2/L1 (<1) times in comparison with the case in the high-resolution measurement mode. Accordingly, the resolving power decreases to about √(L2/L1) in comparison with the resolving power in the high-resolution measurement mode. However, the operation period of the second shutter gate 4 can be shortened. Thus, the sampling rate S2 is increased to L1/L2 (>1) times the sampling rate S1 in the high-resolution measurement mode.

[Zoom-in Measurement Mode]

Figure 4A:
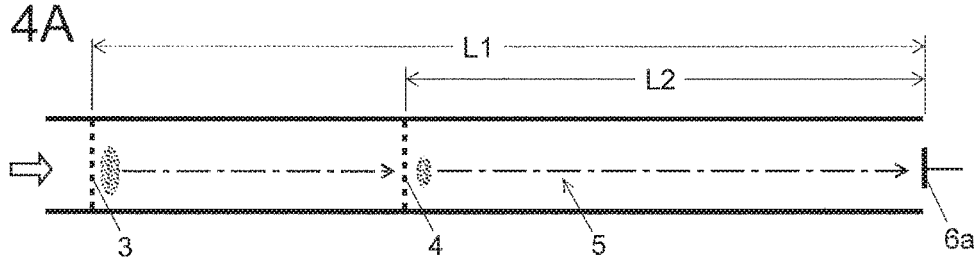
FIG. 4A is a schematic configuration diagram for explaining an operation in the ion mobility spectrometer according to the present embodiment in a zoom-in measurement mode.
Figure 4B:
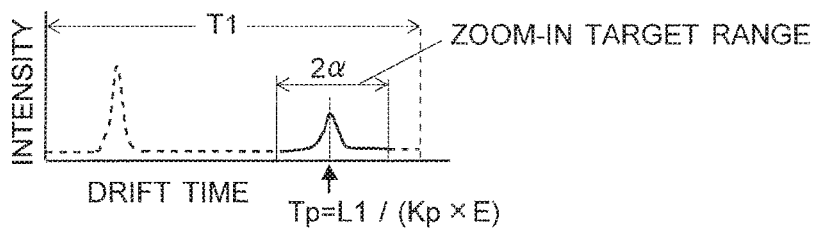
FIG. 4B is a schematic diagram showing an ion mobility spectrum in the zoom-in measurement mode.

FIGS. 4A and 4B are explanatory diagrams for explaining an operation in a zoom-in measurement mode. FIG. 4A is a schematic configuration diagram, and FIG. 4B is a schematic diagram showing an ion mobility spectrum.

When the zoom-in measurement mode is selected using the input unit 10, the user should also appropriately set control conditions, such as the periods of opening/closing operation of the first and second shutter gates 3 and 4 as well as a delay time from a timing at which the first shutter gate 3 is opened to a timing at which the second shutter gate 4 is opened. Instead of allowing the user to enter specify numerical values, the device may be configured to display an ion mobility spectrum obtained, for example, in the high-resolution measurement mode or high sampling-rate measurement mode, allow the user to specify a range of interest, and automatically calculate control conditions according to the specified range.

After these conditions have been specified, the measurement mode switching section 91 in the controller 9 controls the voltage generators 7 and 8 so that the time period during which the first shutter gate 3 is opened and the time period during which the second shutter gate 4 is opened are linked with each other, in a manner as described below. With this control, only ions in an ion group that is the target for the zoom-in measurement and has a specific drift speed (ion mobility) among various ions generated in the ion source 1 are made to drift over the drift length L1 so as to be separated. Ions in other ion groups that are not the target of the zoom-in measurement are blocked at the second shutter gate 4.

If the intensity of the electric field in the drift region 5 is E which is the same as the intensity in the high-resolution measurement mode, and the minimum value of the ion mobility of a molecule to be measured is Kmin, the time T3 required for an ion having the lowest drift speed to pass through the first shutter gate 3 and arrive at the second shutter gate 4 can be expressed as T3=T1×(L1−L2)/L1. If the ion mobility of the ion of interest is Kp (>Kmin), the ion arrives at the second shutter gate 4 at a timing when the period of T3×(Kmin/Kp) passes from the passage of the ion through the first shutter gate 3. Accordingly, the timing at which the shutter gate 4 is opened is made to be delayed by Δ=T3×(Kmin/Kp) from the timing at which the first shutter gate 3 is opened, while the first shutter gate 3 and the second shutter gate 4 are operated at the same sampling rate of 1/T3.

Suppose that the range of ion mobilities to be covered by the zoom-in measurement is 2a (where α≤min (T1−Tp, Tp)). In order to allow ions falling within the aforementioned range to pass through the second shutter gate 4, the second shutter gate 4 is opened at a timing delayed from the first shutter gate 3 by Δ=T3×(Kmin/Kp)−α×(L1−L2)/L1= (Tp−α)×(L1−L2)/L1, where Tp=L1/(Kp×E). In addition, the time width where the second shutter gate 4 is opened is set to be 2α×(L1−L2)/L1. With this, only ions having the ion mobility within the range of 2a pass through the second shutter gate 4, while other ions are blocked. The ions that have passed through the second shutter gate 4 drift to the detector 6. While drifting, the ions are further separated in terms of the ion mobility. As a result, as shown in FIG. 4B, a spectrum which reflects only a portion of the ion mobility spectrum (see FIG. 2B) obtained in the high-resolution measurement mode is obtained.

In this zoom-in measurement mode, the time width during which the first shutter gate 3 is opened affects the resolving power. The time width during which the first shutter gate 3 is opened may be narrowed within a permissible range of the sensitivity. The narrower the time width is, the higher the resolving power becomes. This is the same with the case of the the high-resolution measurement mode. On the other hand, the sampling rate is determined by the operation periods of the first and second shutter gates 3 and 4. For this case, the sampling rate is expressed by S3=1/T3, where T3=T1×(L1−L2)/L1. Accordingly, the sampling rate increases to L1/(L1−L2) times the sampling rate S1=1/T1 in the high-resolution measurement mode. Thus, in the zoom-in measurement mode, although only a limited group of ions can be measured, an ion mobility analysis which zooms in on that ion group can be performed with high resolving power that is comparable to the high-resolution measurement mode. The sampling rate can also be increased.

[Specific Examples of Numerical Values]

As an example of the ion mobility spectrometer according to the above embodiment, consider the case where the second shutter gate 4 is arranged at the center of the drift region 5 (L2=L1/2). In this case, the resolving power decreases to about 1√(2) in the high sampling-rate measurement mode in comparison with the high-resolution measurement mode, but the sampling rate is doubled. Furthermore, if the zoom-in measurement mode is selected, the sampling rate will be doubled while maintaining high resolving power that is comparable to the high-resolution measurement mode.

When the second shutter gate 4 is arranged at a position which satisfies L2<L1/2, the sampling rate in the high sampling-rate measurement mode can be even higher. In the case of the zoom-in measurement mode, although the sampling rate becomes relatively low, the range of ion mobility which can be covered by the zoom-in measurement mode becomes wider and easier to be set.

When the second shutter gate 4 is arranged at a position which satisfies L2>L1/2, the sampling rate in the high sampling-rate measurement mode becomes relatively low, whereas the sampling rate in the zoom-in measurement mode can be even higher. On the contrary, in order to accurately set the range of ion mobility to be covered by the zoom-in measurement mode, it is necessary to switch the opening/closing timings of the second shutter gate 4 at higher speeds.

The aforementioned embodiment is an example of the present invention. It is apparent that any modification, correction, or addition along the scope of the present invention is included in the scope of claims of the present application, in addition to the aforementioned embodiments and various modified embodiments.

For example, although two shutter gates are arranged in the above embodiment, three or more shutter gates can also be arranged. In the above embodiment, ions separated in the drift region 5 are detected by the detector 6. It is also possible, for example, to introduce ions separated in the drift region 5 into a mass separator, such as a quadrupole mass filter, and additionally separate the ions according to their mass-to-charge ratios before detection.

REFERENCE SIGNS LIST

1 . . . Ion Source
2 . . . Drift-Electrode Group
2a . . . Electrode
3 . . . First Shutter Gate
4 . . . Second Shutter Gate
5 . . . Drift Region
6 . . . Detector
6a . . . Detection Electrode
7 . . . Drift Voltage Generator
8 . . . Shutter Voltage Generator
9 . . . Controller
91 . . . Measurement Mode Switching Section
10 . . . Input Unit

The invention claimed is:

1. An ion mobility spectrometer in which ions in a packet-like form are introduced into and made to drifted through a drift region in which an electric field is formed to separate the ions according to their ion mobilities, the ion mobility spectrometer comprising:
  a) a first shutter gate disposed at an entrance of the drift region;
  b) a second shutter gate disposed on a downstream side of the first shutter gate in a drifting direction in the drift region;
  c) a voltage generator for applying predetermined voltages respectively to the first and second shutter gates;
  d) a controller for controlling the voltage generator so as to apply voltages to the first shutter gate and the second shutter gate so that the first shutter gate opens and closes so that ions are made to pass through the first shutter gate in a pulsed form while the second shutter gate remains open so that the ions directly pass through the second shutter gate in a first measurement mode, and the first shutter gate remains open so that ions are made to directly pass through the first shutter gate while the second shutter gate opens and closes so that the ions pass through the second shutter gate in a pulsed form in a second measurement mode;
  e) a drift electrode group configured to form the electric field, the drift electrode group including a plurality of electrodes; and
  f) a detector disposed at an exit of the drift region,
  wherein at least one electrode of the plurality of electrodes is arranged between the second shutter gate and the detector.

2. The ion mobility spectrometer according to claim 1, further comprising an instruction section for instructing the controller to select at least one of the first measurement mode and the second measurement mode, wherein:
  the controller performs a control corresponding to the first measurement mode or the second measurement mode according to a selection instruction by the instruction section.

3. The ion mobility spectrometer according to claim 1, wherein:
  a third measurement mode is provided in addition to the first and the second measurement mode, and the controller in the third measurement mode controls the voltage generator to apply voltages to the first shutter gate and the second shutter gate so the first shutter gate and the second shutter gate open and close so that the first shutter gate makes ions pass through in the pulsed form, and the second shutter gate makes ions pass through in the pulsed form for a predetermined time period after the passage of a predetermined time period from a time point when the first shutter gate is opened,
  wherein the first shutter gate opens and closes at a delayed timing from the timing at which the second shutter gate opens and closes, and
  wherein the second shutter gate opens and closes at a delayed timing from the timing at which the first shutter gate opens and closes.

4. The ion mobility spectrometer according to claim 2, wherein:
  a third measurement mode is provided in addition to the first and the second measurement mode, and the controller in the third measurement mode controls the voltage generator to apply voltages to the first shutter gate and the second shutter gate so the first shutter gate and the second shutter gate open and close so that the first shutter gate makes ions pass through in the pulsed form, and the second shutter gate makes ions pass through in the pulsed form for a predetermined time period after the passage of a predetermined time period from a time point when the first shutter gate is opened,
  wherein the first shutter gate opens and closes at a delayed timing from the timing at which the second shutter gate opens and closes, and
  wherein the second shutter gate opens and closes at a delayed timing from the timing at which the first shutter gate opens and closes.

5. The ion mobility spectrometer according to claim 1, wherein more than one of the electrodes of the plurality of electrodes are arranged between the second shutter gate and the detector.

* * * * *